(12) United States Patent
Suib et al.

(10) Patent No.: US 8,987,160 B2
(45) Date of Patent: Mar. 24, 2015

(54) FISCHER-TROPSCH CATALYSTS CONTAINING IRON OR COBALT SELECTIVE TOWARDS HIGHER HYDROCARBONS

(75) Inventors: Steven L. Suib, Storrs, CT (US); Boxun Hu, Storrs, CT (US); Eric Rolland Kreidler, Pickerington, OH (US); Christopher James Brooks, Dublin, OH (US)

(73) Assignees: Honda Motor Co., Ltd., Tokyo (JP); The University of Connecticut, Farmington, CT (US)

( * ) Notice: Subject to any disclaimer, the term of this patent is extended or adjusted under 35 U.S.C. 154(b) by 496 days.

(21) Appl. No.: 13/072,683

(22) Filed: Mar. 26, 2011

(65) Prior Publication Data

US 2012/0245236 A1    Sep. 27, 2012

(51) Int. Cl.
| | |
|---|---|
| *B01J 29/06* | (2006.01) |
| *B01J 23/34* | (2006.01) |
| *B01J 27/22* | (2006.01) |
| *B01J 35/00* | (2006.01) |
| *B01J 23/889* | (2006.01) |
| *B01J 37/02* | (2006.01) |
| *B01J 37/16* | (2006.01) |
| *B01J 37/18* | (2006.01) |
| *C10G 2/00* | (2006.01) |
| *C07C 51/367* | (2006.01) |

(52) U.S. Cl.
CPC ............... *B01J 35/002* (2013.01); *B01J 23/34* (2013.01); *B01J 23/8892* (2013.01); *B01J 27/22* (2013.01); *B01J 37/0201* (2013.01); *B01J 37/16* (2013.01); *B01J 37/18* (2013.01); *C10G 2/33* (2013.01); *C10G 2/332* (2013.01); *C10G 2/334* (2013.01); *C07C 51/367* (2013.01); *B01J 2203/063* (2013.01); *B01J 2229/183* (2013.01); *B01J 2229/186* (2013.01)
USPC ................. 502/60; 502/73; 502/74; 502/177; 502/324

(58) Field of Classification Search
USPC ................................. 502/60, 73, 74, 324, 177
See application file for complete search history.

(56) References Cited

U.S. PATENT DOCUMENTS

| | | | |
|---|---|---|---|
| 4,687,784 A | 8/1987 | Foley et al. | |
| 5,597,944 A | 1/1997 | O'Young et al. | |
| 5,702,674 A | 12/1997 | O'Young et al. | |
| 6,114,399 A | 9/2000 | Roberts et al. | |
| 6,491,880 B1 | 12/2002 | Wang et al. | |
| 6,656,343 B2 | 12/2003 | Dancuart | |
| 6,756,411 B2 | 6/2004 | Betts et al. | |
| 6,822,008 B2 | 11/2004 | Srinivasan et al. | |
| 6,835,690 B2 | 12/2004 | Van Berge et al. | |
| 6,846,848 B2 | 1/2005 | Wittenbrink et al. | |
| 6,897,177 B2 | 5/2005 | Van Berge et al. | |
| 6,982,287 B2 | 1/2006 | Wang et al. | |
| 6,992,113 B2 | 1/2006 | O'Rear et al. | |
| 7,157,404 B1 | 1/2007 | Jun et al. | |
| 7,262,225 B2 | 8/2007 | Van Berge et al. | |
| 7,355,075 B2 | 4/2008 | Sithambaram et al. | |
| 7,393,876 B2 | 7/2008 | White et al. | |
| 7,438,887 B2 | 10/2008 | Suib et al. | |
| 7,524,787 B2 | 4/2009 | Visagie et al. | |
| 7,678,952 B2 | 3/2010 | Dupain et al. | |
| 7,767,770 B2 | 8/2010 | Han et al. | |
| 2008/0015267 A1 | 1/2008 | Lu et al. | |
| 2008/0207959 A1 | 8/2008 | Plante et al. | |
| 2010/0088951 A1 | 4/2010 | White et al. | |

FOREIGN PATENT DOCUMENTS

| | | |
|---|---|---|
| EP | 0 446 035 A2 | 9/1991 |
| EP | 2 165 997 A1 | 3/2010 |
| WO | 95/25693 A1 | 9/1995 |

OTHER PUBLICATIONS

Zhang, Cheng-Hau, et al., "Study of an iron-manganese Fischer-Tropsch synthesis catalyst promoted with copper," J. Catalysis, vol. 237, No. 2, pp. 405-415, Jan. 25, 2006, Elsevier.

(Continued)

*Primary Examiner* — Elizabeth Wood
(74) *Attorney, Agent, or Firm* — Capitol City TechLaw, PLLC; Mark E. Duell; Samuel P. Burkholder

(57) ABSTRACT

Cryptomelane-type manganese oxide octahedral molecular sieves (OMS-2) supported Fe and Co catalysts are utilized in a method for producing hydrocarbons by a Fischer-Tropsch mechanism. The hydrocarbon producing method includes providing a catalyst of a manganese oxide-based octahedral molecular sieve nanofibers with an active catalyst component of at least one of iron, cobalt, nickel, copper, manganese, vanadium, zinc, and mixtures thereof, and further containing an alkali metal. The formation of iron carbides and cobalt carbides by exposing the catalyst to conditions sufficient to form those carbides is also taught. After the catalyst has been appropriately treated, a carbon source and a hydrogen source are provided and contacted with the catalyst to thereby form a hydrocarbon containing product. The catalyst have high catalytic activity and selectivity (75%) for C2+ hydrocarbons in both CO hydrogenation and CO2 hydrogenation. Highly selective syntheses of high value jet fuel, C2-C6 alkenes, C2-C6 carboxylic acids; α-hydroxylic acids and their derivatives have been realized by tuning the oxidation ability of OMS-2 supports and by doping with $Cu^{2+}$ ions.

21 Claims, 15 Drawing Sheets

(56) References Cited

OTHER PUBLICATIONS

Bezemer, G. Leendert, Johannes H. Bitter, Herman P. C. E. Kuipers, Heiko Oosterbeek, Johannes E. Holewijn, Xiaoding Xu, Freek Kapteijn, A. Jos van Dillen, and Krijn P. de Jong. 2006. "Cobalt Particle Size Effects in the Fischer—Tropsch Reaction Studied with Carbon Nanofiber Supported Catalysts." J. Am. Chem. Soc. vol. 128, pp. 3956-3964.

Arslan, Ilke, John C. Walmsley, Erling Rytter, Edvard Bergene, and Paul A. Midgeley. 2008. "Toward Three-Dimensional Nanoengineering of Heterogeneous Catalysts." J. Am. Chem. Soc. vol. 130, pp. 5716-5719.

Chan, Bun and Leo Radom. 2006. "Design of Effective Zeolite Catalysts for the Complete Hydrogenation of $CO_2$." J. Am. Chem. Soc. vol. 128, pp. 5322-5323.

Choi, Pyoung Ho, Ki-Won Jun, Soo-Jae Lee, Myuong-Jae Choi, and Kyu-Wan Lee. 1996. "Hydrogenation of Carbon Dioxide over Alumina Supported Fe—K Catalysts." Catalysis Letters. vol. 40, pp. 115-118.

Fisher, Ian A. and Alexis T. Bell. 1996. "A Comparative Study of CO and $CO_2$ Hydrogenation over $Rh/SiO_2$." Journal of Catalysis. vol. 162, pp. 54-65, Article No. 0259.

Znak, Leszek, Zbigniew Kaszkur, and Jerzy Zielinski. 2010. "Evolution of Metal Phase in the Course of CO Hydrogenation on Potassium Promoted $Ni/Al_2O_3$ Catalyst." Catalysis Letters. vol. 136, pp. 92-95.

Schunemann, V., H. Trevino, G. D. Lei, D. C. Tomczak, W. M. H. Sachtler, K. Fogash, and J. A. Dumesic. 1995. "Fe Promoted Rh-Clusters in Zeolite NaY: Characterization and Catalytic Performance in CO Hydrogenation." Journal of Catalysis. vol. 153, pp. 144-157.

Chen, Wei, Xiulian Pan, Marc-Georg Willinger, Dang Sheng Su, and Xinhe Bao. 2006. "Facile Autoreduction of Iron Oxide/Carbon Nanotube Encapsulates." J. Am. Chem. Soc. vol. 128, pp. 3136-3137.

Li, Tingzhen, Yong Yang, Chenghua Zhang, Zhichao Tao, Haijun Wan, Xia An, Hongwei Xiang, and Yongwang Li. 2007. "Effect of Manganese Incorporation Manner on an Iron-Based Catalyst for Fischer-Tropsch Synthesis." Journal of Natural Gas Chemistry. vol. 16, pp. 244-251.

Suib, Steven L. Apr. 2008. "Porous Manganese Oxide Octahedral Molecular Sieves and Octahedral Layered Materials." vol. 41, No. 4, pp. 479-487.

Cai, Jun, Jia Liu, William S. Willis, and Steven L. Suib. 2001. "Framework Doping of Iron in Tunnel Structure Cryptomelane." Chem. Mater. vol. 13, pp. 2413-2422.

Hu, Boxun, Chun-hu Chen, Samuel J. Frueh, Lei Jin, Raymond Joesten, and Steven L. Suib. 2010. "Removal of Aqueous Phenol by Adsorption and Oxidation with Doped Hydrophobic Cryptomelane-Type Manganese Oxide (K—OMS-2) Nanofibers." J. Phys. Chem. C. vol. 114, pp. 9835-9844.

Sun, Shouli, Kaoru Fujimoto, Yi Zhang, and Noritatsu Tsubaki. 2003. "A Highly Active and Stable Fischer-Tropsch Synthesis Cobalt/Silica Catalyst with Bimodal Cobalt Particle Distribution." Catalysis Communications. vol. 4, pp. 361-364.

Suib, Steven L. 2008. "Structure, Porosity, and Redox in Porous Manganese Oxide Octahedral Layer and Molecular Sieve Materials." Journal of Materials Chemistry. vol. 18, pp. 1623-1631.

de Smit, Emiel, Ingmar Swart, J. Fredrik Creemer, Gerard H. Hoveling, Mary K. Gilles, Tolek Tyliszczak, Patricia J. Kooyman, Henny W. Zandbergen, Cynthia Morin, Bert M. Weckhuysen, and Frank M. F. de Groot. Nov. 13, 2008. "Nanoscale Chemical Imaging of a Working Catalyst by Scanning Transmission X-Ray Microscopy." Nature. vol. 456, pp. 222-225.

Somorjai, Gabor A., Heinz Frei, and Jeong Y. Park. 2009. "Advancing the Frontiers in Nanocatalysis, Biointerfaces, and Renewable Energy Conversion by Innovations of Surface Techniques." J. Am. Chem. Soc. vol. 131, pp. 16589-16605.

Harranz, Tirma, Sergio Rojas, Francisco J. Perez-Alonso, Manuel Ojeda, Pilar Terreros, and Jose Luis G. Fierro. 2006. "Genesis of Iron Carbides and Their Role in the Synthesis of Hydrocarbons from Synthesis Gas." Journal of Catalysis. vol. 243, pp. 199-211.

Yuan, Jikang, Kate Laubernds, Josanlet Villegas, Sinue Gomez, and Steven L. Suib. Oct. 4, 2004. "Spontaneous Formation of Inorganic Paper-Like Materials." Advanced Materials. vol. 16, No. 19, pp. 1729-1732.

Visconti, Carlo Giorgio, Luca Lietti, Enrico Tronconi, Pio Forzatti, Roberto Zennaro, and Elisabetta Finocchio. 2009. "Fischer-Tropsch Synthesis on a $Co/Al_2O_3$ Catalyst with $CO_2$ Containing Syngas." Applied Catalysis A: General. vol. 355, pp. 61-68.

Zhang, Yongqing, Gary Jacobs, Dennis E. Sparks, Mark E. Dry, and Burtron H. Davis. 2002. "CO and $CO_2$ Hydrogenation Study on Supported Cobalt Fischer-Tropsch Synthesis Catalysts." Catalysis Today. vol. 71, pp. 411-418.

Yin, Yuan-Gen, Wen-Qing Xu, Roberto DeGuzman, Steven L. Suib, and C. L. O'Young. 1994. "Studies of Stability and Reactivity of Synthetic Cryptomelane-like Manganese Oxide Octahedral Molecular Sieves." Inorganic Chemistry. vol. 33, No. 19, pp. 4384-4389.

Liu, Ying, Cheng-Hua Zhang, Yu Wang, Ying Li, Xu Hao, Liang Bai, Hong-Wei Xiang, Yuan-Yuan Xu, Bing Zhong, and Yong-Wang Li. 2008. "Effect of Co-feeding Carbon Dioxide on Fischer-Tropsch Synthesis over an Iron-Manganese Catalyst in a Spinning Basket Reactor." Fuel Processing Technology. vol. 89, pp. 234-241.

Morales, Fernando, Frank M.F. de Groot, Onno L.J. Gijzeman, Ad Mens, Odile Stephan, and Bert M. Weckhuysen. 2005. "Mn Promotion Effects in $Co/TiO_2$ Fischer-Tropsch Catalysts as Investigated by XPS and STEM-EELS." Journal of Catalysis. vol. 230, pp. 301-308.

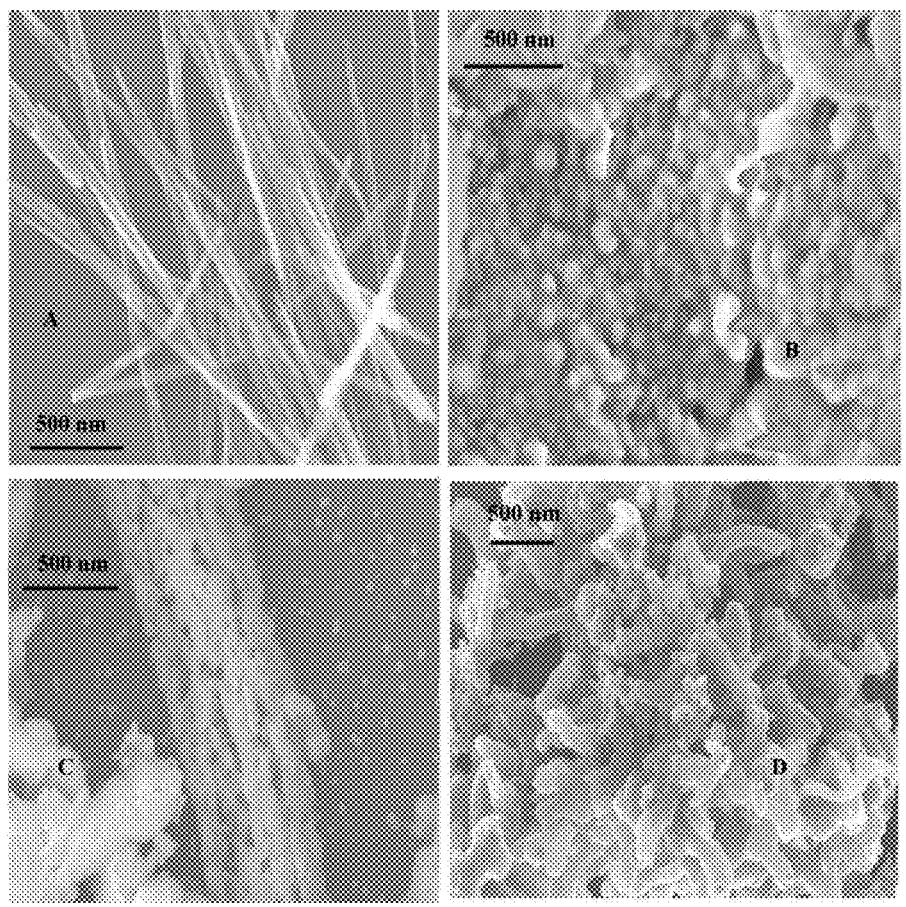
Fig. 1. FESEM images of K-OMS-2 supports (A) and post-reaction CAT A (B), CAT C (C), and black deposit from *in situ* XRD study of CAT C (D)

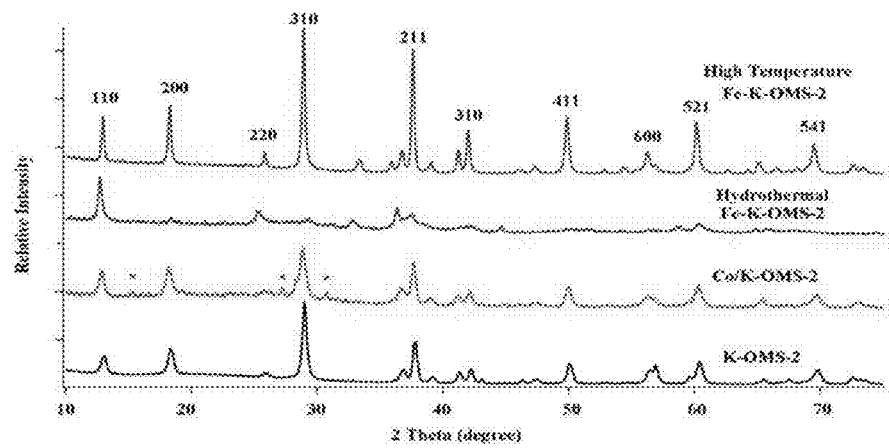
Fig. 2. XRD patterns of the supported Fe and Co catalysts. "*" represents $\alpha\text{-Co}(NO_3)_2\cdot 6H_2O$.

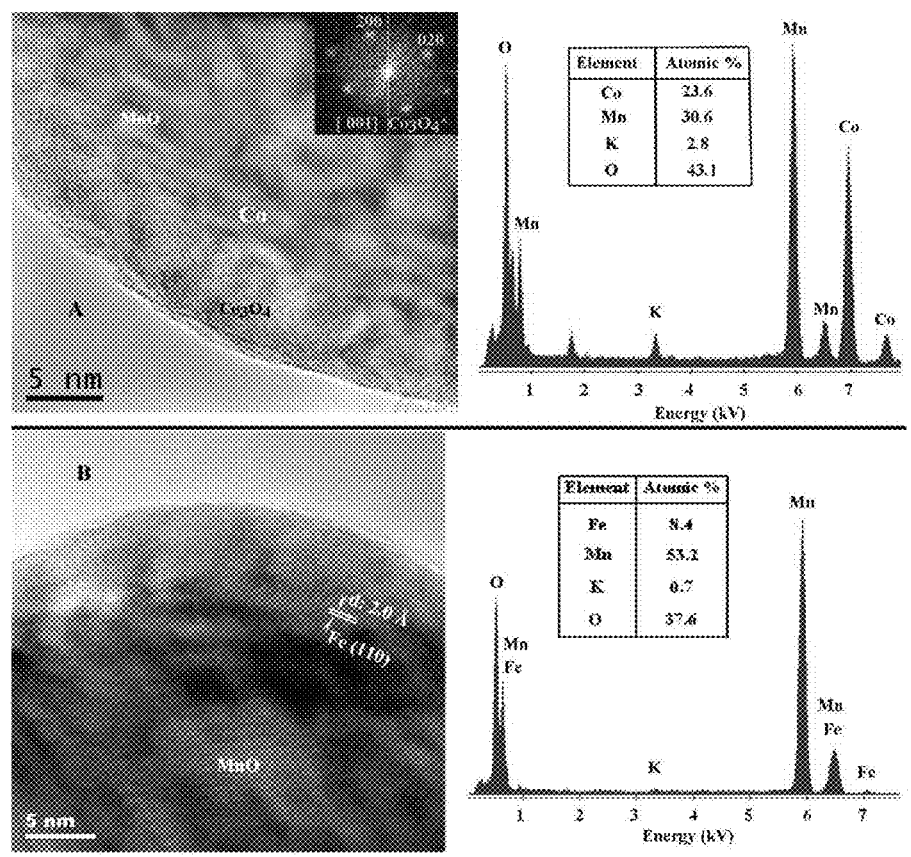
Fig. 3. TEM images and EDS spectra of the reduced CAT A (A) and CAT D (B) catalysts. The insert tables are the TEM-EDS results.

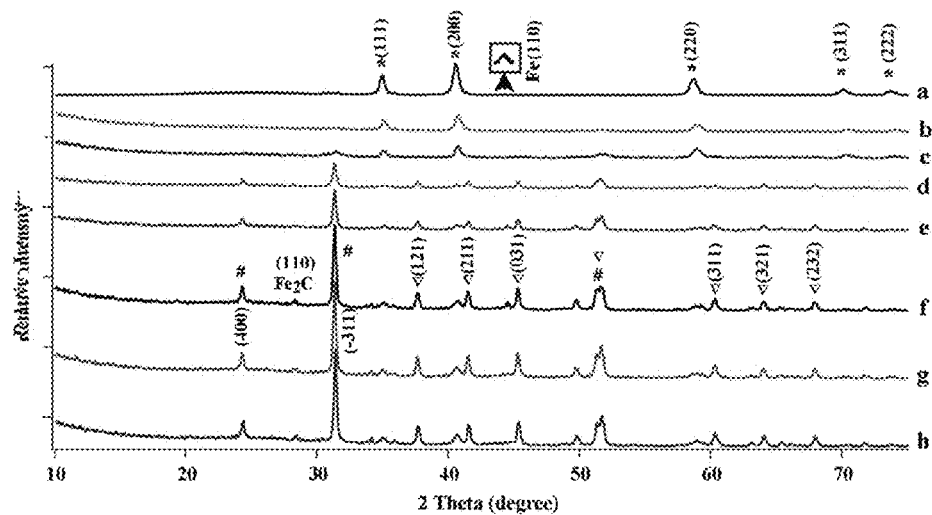
Fig. 4. The *in situ* XRD patterns of CAT C in CO hydrogenation. "*": MnO, "#": $KHCO_3$; "∇": $Fe_3C$.

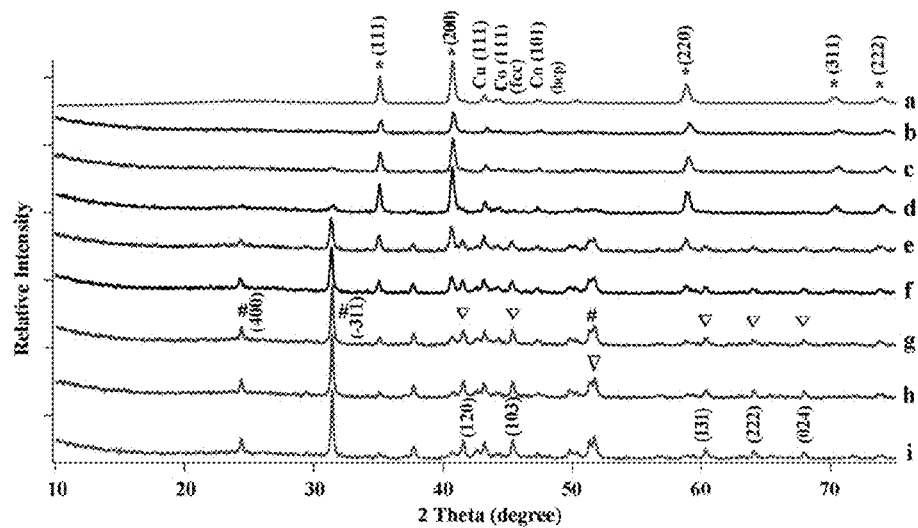
Fig. 5. *In situ* XRD patterns of CAT A in the hydrogenation of CO. "*": MnO, "#": KHCO$_3$; "∇": Co$_3$C.

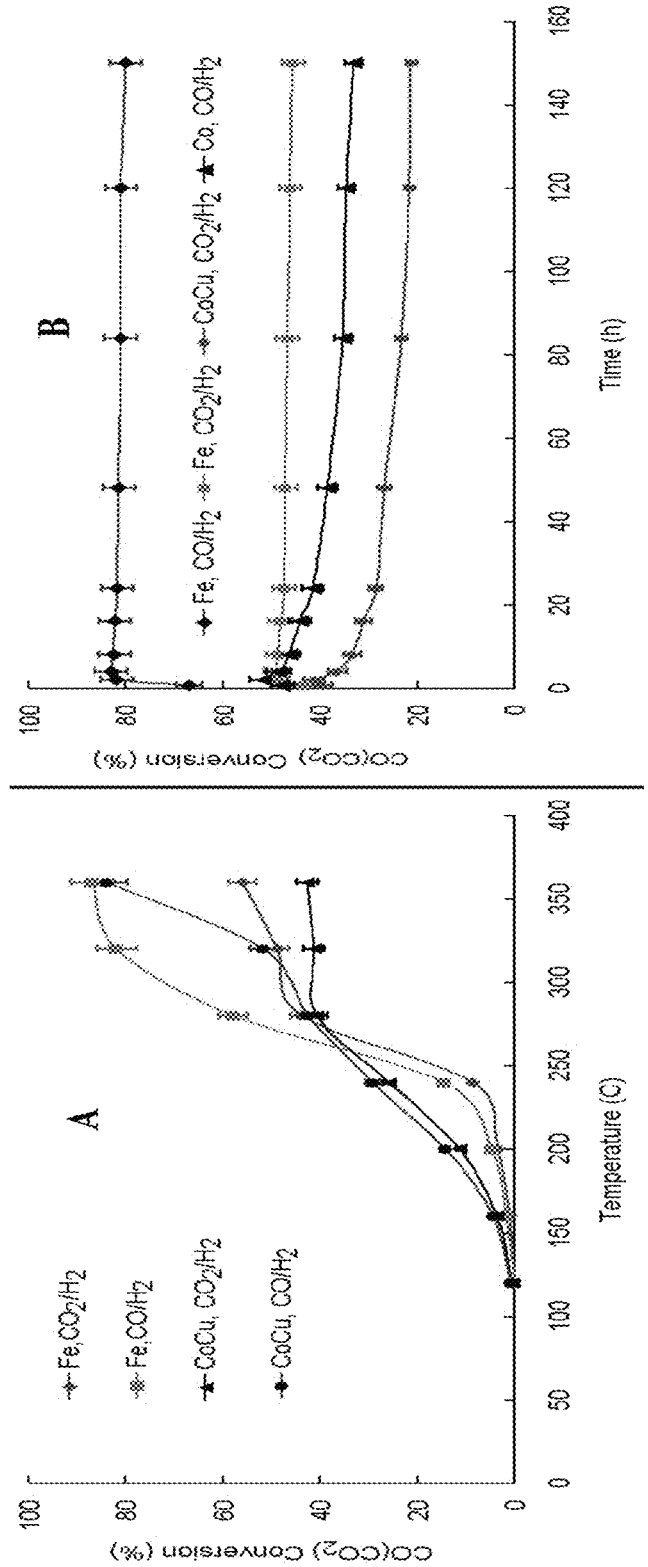
Fig. 6. Activity-temperature relationship (A) and stability at 320°C (B) of the OMS-2 Fe (CAT C) and CoCu (CAT A) for $CO_2/CO$ hydrogenation.

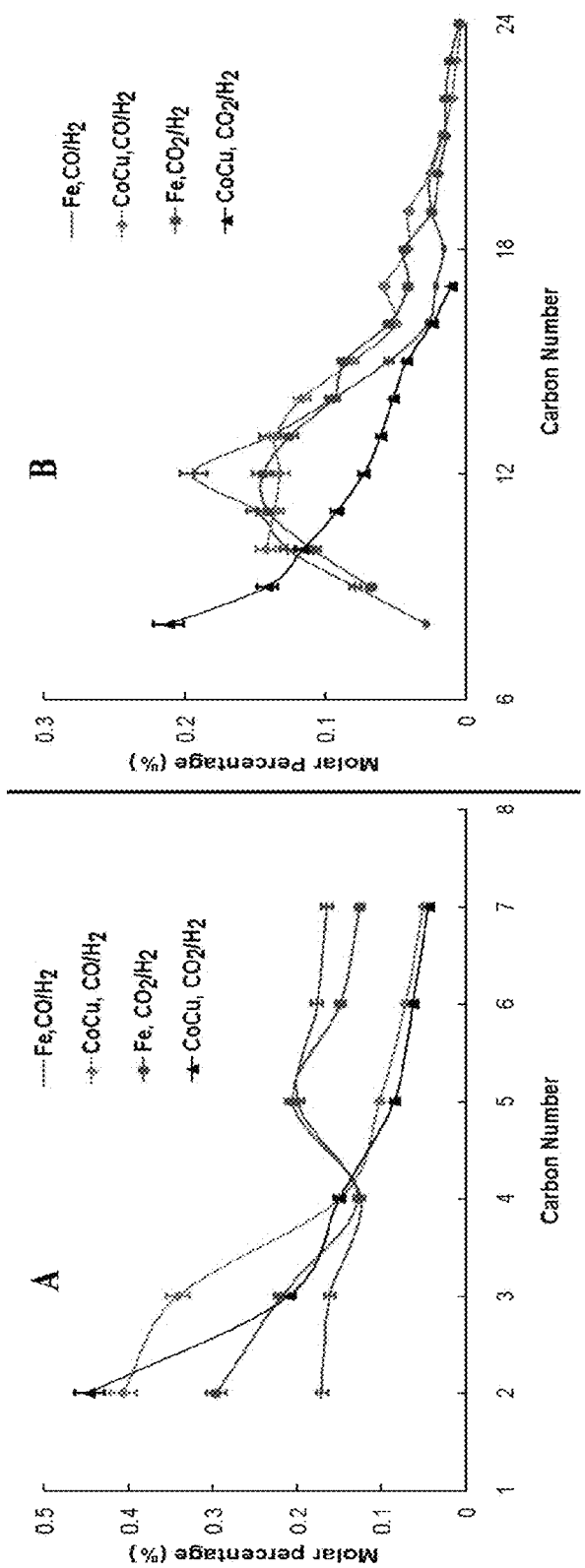
Fig. 7. Chain length for CO/CO$_2$ hydrogenation for OMS-2 Co (CAT A) and Fe (CAT C). A: GC gas analysis. B: GC-MS liquid analysis.

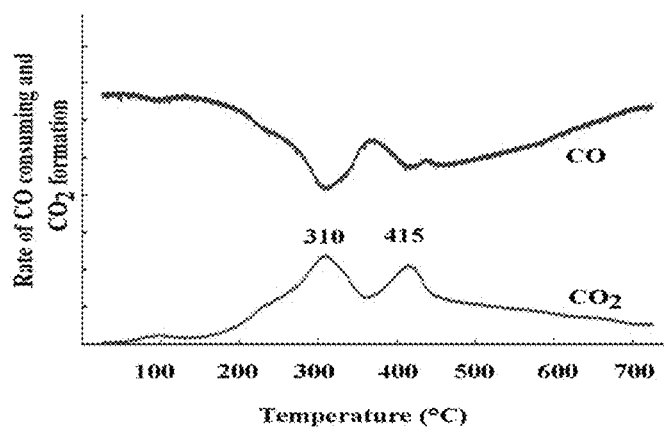
Fig. 8. TPR-MS spectra of K-OMS-2 with 5% CO/$H_2$ (balance).

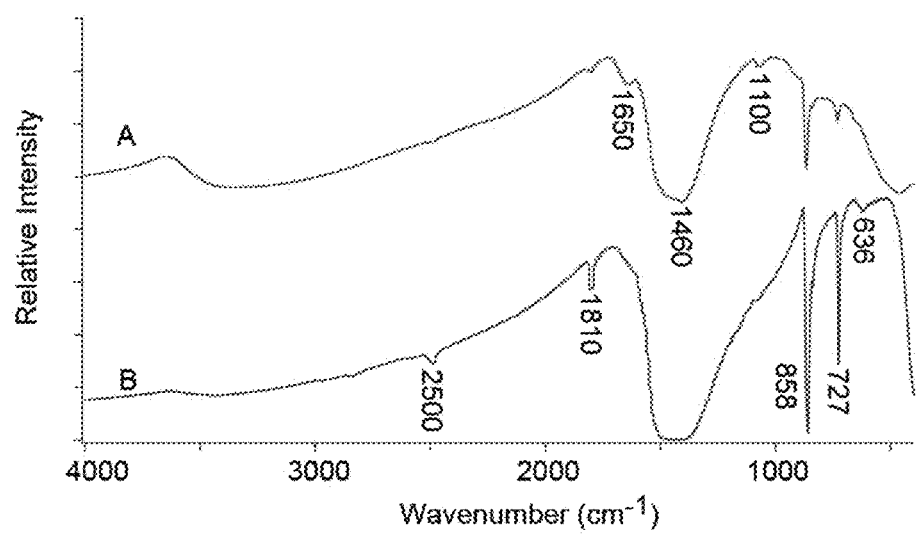
Fig. 9 FT-IR of OMS-2 catalysts CAT C (A above) and CAT A (B above).

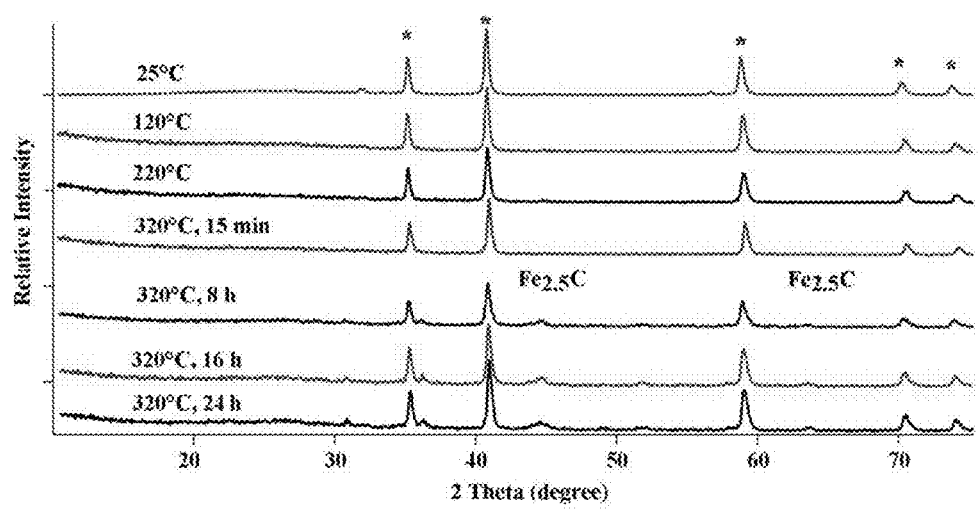
Fig. 10. *In situ* XRD of supported Fe catalysts in $CO_2$ hydrogenation. "*" represents MnO.

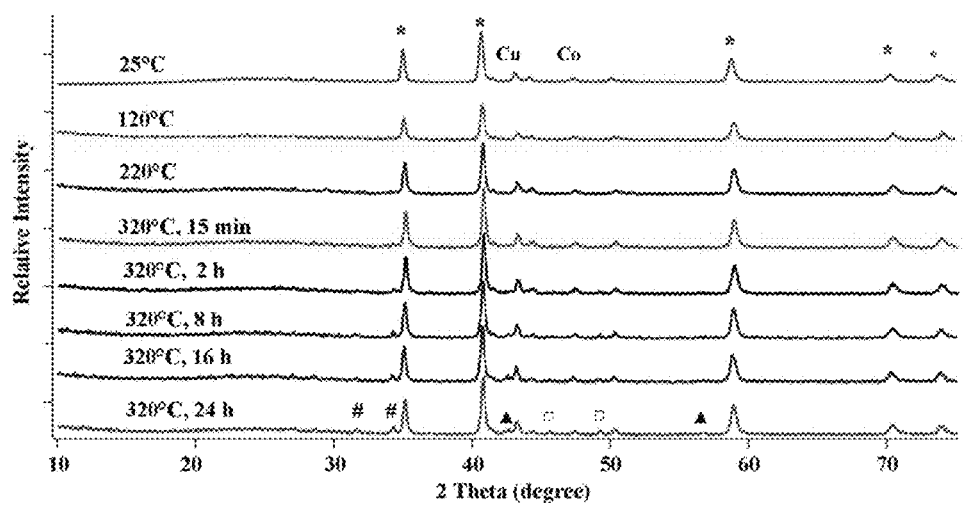
Fig. 11. *In situ* XRD of supported Co catalysts in $CO_2$ hydrogenation.
"*": MnO, "#": $KHCO_3$, "▲": $Co_2C$, "□": $Co_3C$.

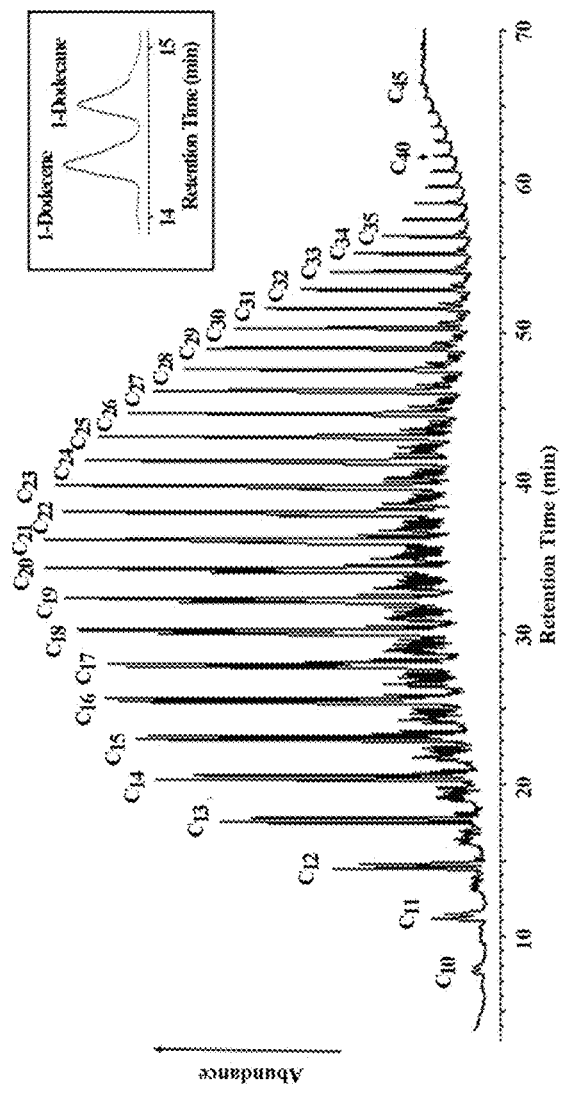
Fig. 12. GC-MS of the MnO supported Co catalysts in CO hydrogenation at 280°C.
Inset - two $C_{12}$ peaks enlarged.

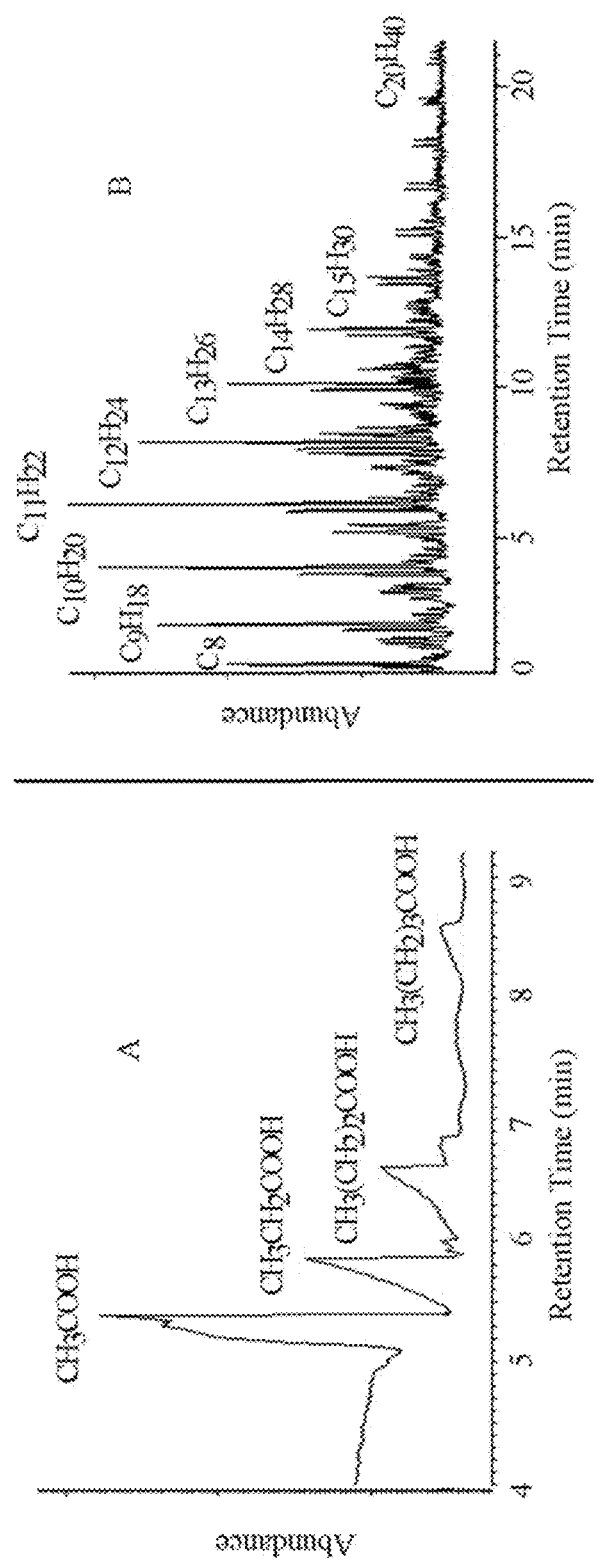
Fig. 13. Liquid products distribution of $CO_2$ hydrogenation after CO reduction; A: CAT B at 350°C, B: CAT C at 450°C.

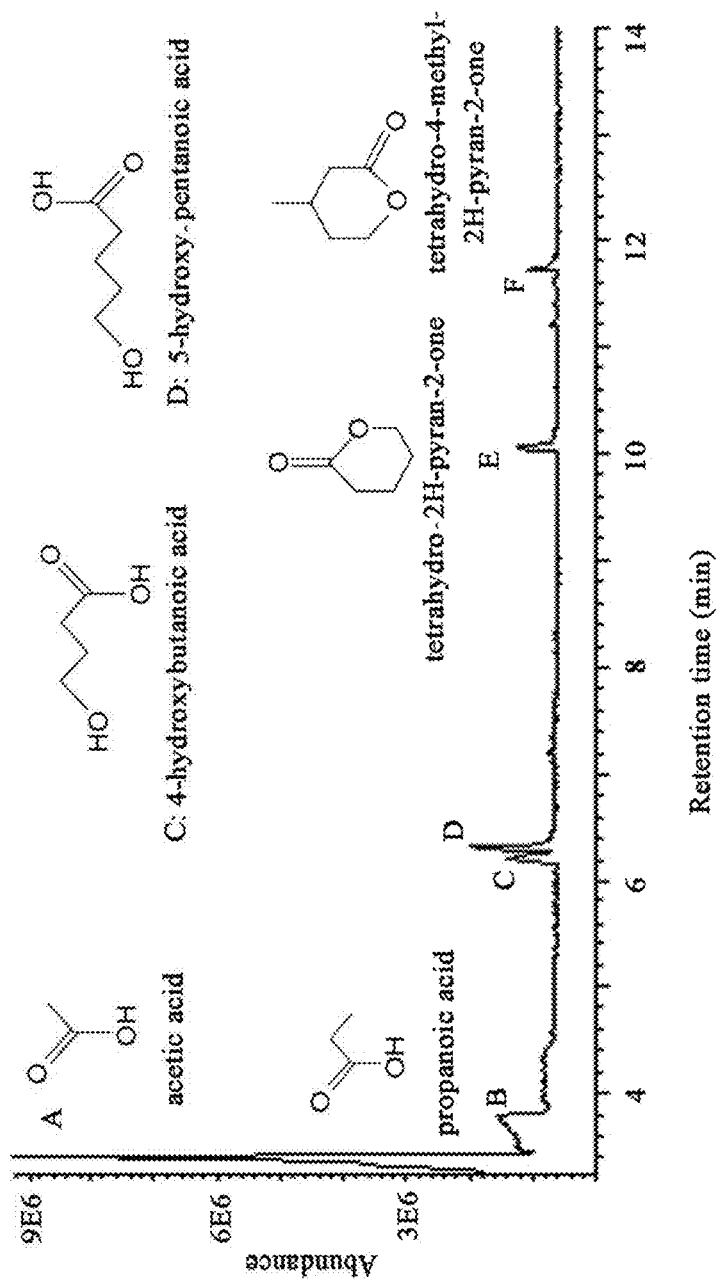
Fig. 14. Liquid products distribution of CAT A.

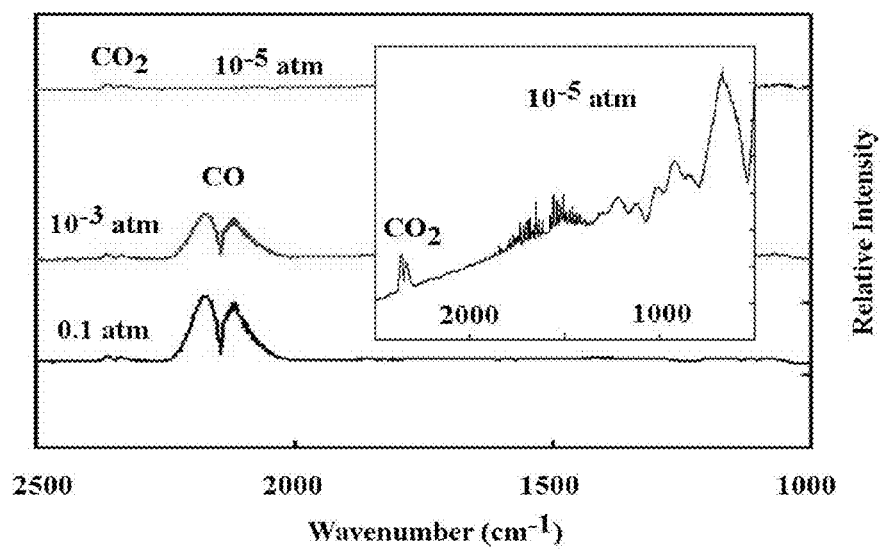
Fig. 15. *In situ* FT-IR spectra OMS-2 Fe and Co catalysts CO hydrogenation at 1 atm. Inset: enlarged spectrum at $10^{-5}$ atm.

FISCHER-TROPSCH CATALYSTS CONTAINING IRON OR COBALT SELECTIVE TOWARDS HIGHER HYDROCARBONS

RELATED APPLICATIONS

This application is related to U.S. Provisional Patent Application No. 61/467,979 entitled "Materials and Design for an Electrocatalytic Device which Produces Hydrocarbon Transportation Fuels" naming as inventors Suib et al. filed on the same date as the present application, and to U.S. patent application Ser. No. 13/430,209, filed on Mar. 26, 2012, the entire disclosures of which are incorporated by reference for all purposes.

BACKGROUND

1. Field of the Invention

The present teachings are directed towards a method for producing hydrocarbons by a Fischer-Tropsch mechanism and the catalysts for the method. The hydrocarbon producing method includes providing a catalyst of a manganese oxide-based octahedral molecular sieve nanofibers with at least one of iron, cobalt, nickel, copper, manganese, vanadium, zinc, and mixtures thereof, and further containing an alkali metal. The formation of iron carbides and cobalt carbides by exposing the catalyst to conditions sufficient to form those carbides is also taught. After the catalyst has been appropriately treated, a carbon source and a hydrogen source are provided and contacted with the catalyst to thereby form a hydrocarbon containing product. The characteristics of the hydrocarbon products can be controlled by the formulation and treatment of the catalyst.

2. Discussion of the Related Art

Production of clean fuel and fine chemicals via Fischer-Tropsch ("FT") synthesis has attracted interest in both academia and industry. Catalysts (Co, Fe, Ru, and Ni) for the conversion of $CO_2$ supported on inert silica, alumina, zeolites, and carbon nanotubes have been developed for FT synthesis. The hydrocarbon products of these catalysts are mainly paraffins. Additional manganese oxides have been used to increase the selectivity towards long chain olefins, for instance, alkenes, but these manganese oxides decreased overall activity due to their enrichment on the catalyst surfaces.

K-OMS-2 ($KMn^{3+}Mn^{4+}_7O_{16}$) is composed of 2×2 edge-shared $MnO_6^-$ octahedral chains, which are corner shared to form one-dimensional tunnels (4.6×4.6 A), with $K^+$ ions located in the tunnels. The unique expandable structure and components suggest that K-OMS-2 nanofibers can be suitable templates for engineering design of FT catalysts. The high surface area, 60-150 $m^2/g$ OMS-2 nanofibers can be supports for incipient wetness impregnation ("IWI") of Co, Fe, and Cu-based catalysts. Additionally, the mixed valence K-OMS-2 structure can be selective oxidation catalysts.

SUMMARY

The present disclosure teaches a catalyst based on manganese oxide-based octahedral molecular sieve nanofibers, (also known as synthetic cryptomelane), an active catalyst metal of at least one of iron, cobalt, nickel, copper, manganese, vanadium, zinc, and mixtures thereof, and an alkali metal typically present as a promoter. In some embodiments of the catalyst, the active catalyst metals are present as phases of iron carbide or cobalt carbide.

A method for producing hydrocarbons by an FT mechanism from CO and/or $CO_2$ hydrogenation is also disclosed herein. This method can include providing a catalyst composed of a manganese oxide-based octahedral molecular sieve nanofiber, at least one of iron, cobalt, nickel, copper, manganese, vanadium, zinc, and mixtures thereof, and an alkali metal. The method also features the formation of iron carbides and cobalt carbides by exposing the catalyst to conditions sufficient to form those carbides. After the catalyst has been appropriately treated, a carbon source and a hydrogen source are provided and contacted with the catalyst to thereby form the desired hydrocarbon containing product.

The presently disclosed OMS-2 supported Co and Fe catalysts can be utilized for the highly selective and efficient production of jet fuel, alkenes, $C_2$-$C_6$ carboxylic acids, α-hydroxylic acids, and their derivatives via $CO_2$ and CO hydrogenation under different conditions. Neither of the OMS-2 supported Fe, Co, and Co/Cu catalysts formulations for FT synthesis nor the selective production method of the high value hydrocarbons by adjusting the oxidation ability of K-OMS-2 supports have been previously disclosed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIGS. 1A-1D illustrate the FESEM micrographs;

FIG. 2 illustrates XRD patterns;

FIGS. 3A and 3B illustrate TEM and EDS spectra;

FIG. 4 illustrates in situ XRD patterns at various aging conditions as follows a: CAT C reduced in $H_2$/He at 450° C., then b-d catalysts in F-T reaction at different temperatures. b: 120° C., c: 220° C., d: 320° C. (15 min), e-h: F-T reaction for different times at 320° C. e: 2 h, f: 8 h, g: 16 h, h: 24 h;

FIG. 5 illustrates in situ XRD patterns;

FIG. 6 illustrates CO/CO2 conversion activity time-on-stream stability at the following reaction conditions: gas hourly space velocities (GHSV): 7200 $cm^3$/(h.g catalyst), $CO_2$(CO)/$H_2$ molar ratio=0.5, pressure=13.6 atm;

FIG. 7 illustrates distribution of hydrocarbon by carbon number, the reaction conditions are the same as in Table 2;

FIG. 8 illustrates TPR-MS spectra;

FIG. 9 illustrates FT-IR spectra after CO hydrogenation, infrared peaks at 2500 and 1100 $cm^{-1}$ are assigned to $HCO^{3-}$ ions, and the bands at 1810, 1460, and 856 $cm^{-1}$ are assigned to $CO_3^{2-}$ groups, and the band at 727 $cm^{-1}$ is assigned to out of plane bending of OH groups;

FIG. 10 illustrates in situ XRD patterns;

FIG. 11 illustrates in situ XRD patterns;

FIG. 12 illustrates GC-MS spectra, the catalysts contained 30 wt. % Co, and the reaction conditions were: gas hourly space velocities (GHSV): 2400$cm^3$/(h.g catalyst), CO/$H_2$ molar ratio =0.5, pressure=13.6 atm;

FIG. 13 illustrates distribution of hydrocarbon products, and the effect of CO reduction temperatures on $CO_2$ hydrogenation, the reaction conditions were: GHSV: 7200 $cm^3$/(h.g catalyst), $CO_2$(CO)/$H_2$ molar ratio=0.5, pressure=13.6 atm, and temperature: 280° C.;

FIG. 14 illustrates distribution of hydrocarbon products, and the reaction conditions were: GHSV: 7200 $cm^3$/(h.g catalyst), $CO_2$(CO)/$H_2$ molar ratio=0.5, pressure=13.6 atm, and temperature: 320° C., and FIG. 15 illustrates in situ FT-IR spectra of typical OMS-2 supported Fe and Co catalysts in CO hydrogenation at a temperature of 320° C. and a pressure of 1 atm. The inset figure is an enlarged spectrum at a pressure of $10^{-5}$ atm. After degassing at $10^{-5}$ atm, the in situ FT-IR spectra show only $CO_2$ adsorbed on the catalysts. This indicates $CO_2$ adsorption on these catalysts is stronger than CO adsorption.

DETAILED DESCRIPTION

Disclosed in the present application is a catalyst for producing hydrocarbons by means of the FT reaction mechanism, the catalyst can be composed of manganese oxide-based octahedral molecular sieve nanofibers, at least one of iron, cobalt, nickel, copper, manganese, vanadium, zinc, and mixtures thereof, and an alkali metal. Generally, iron-containing catalysts will have iron present in one or more iron carbide phases, and cobalt-containing catalysts will have cobalt present in one of more cobalt carbide phases. Carbide phases include, for example, $Fe_2C$, $Fe_{2.5}C$, $Fe_3C$, $Co_2C$, and $Co_3C$. The preferred carbides for each metal are the $Fe_3C$ and the $Co_3C$ phases, respectively.

In some embodiments, the alkali metal can be potassium, and it can be present in an amount ranging from about 0.5 wt. % to about 7.5 wt. %, or an amount ranging an amount ranging from about 4.0 wt. % to about 6.0 wt. %. Preferably, the potassium is present as potassium hydrogen carbonate.

In those embodiments where the catalyst contains a mixture of cobalt and copper, the copper can be present at a Cu:Co molar ratio ranging from about 0.01:1 to about 0.5:1.

In those iron-containing embodiments, the catalyst can have iron present at a Fe:Mn molar ratio of no greater than about 1:5.

The alkali metal should be present, in the presently disclosed catalyst, at an alkali metal:Mn molar ratio of no greater than about 1:8.

The presently disclosed catalyst can include manganese present not only in the manganese oxide-based octahedral molecular sieve support material but also as manganese added via any suitable impregnation or deposition method to the surface of the OMS-2 support to provide a catalytic functionality, either as a catalyst or as a catalyst promoter or modifier.

The catalysts according to the present disclosure can have the active catalyst species present on the surface of the molecular sieve support material or the catalyst species can be incorporated into the lattice framework of the molecular sieve support material, and in some cases the catalyst species can be present in both locations. Known impregnation and/or deposition methods, such as IWI or CVD, can be utilized to achieve the desired placement of the catalyst species. In some cases of the present catalyst, the catalyst species can be initially impregnated or deposited on the surface of the molecular sieve, and can then migrate to positions within the lattice itself under reaction conditions. Furthermore, the molecular sieve material can be synthesized with the catalyst species directly incorporated into the lattice framework during the synthesis.

The present disclosure also teaches a method for producing hydrocarbons comprising providing a catalyst containing a manganese oxide-based octahedral molecular sieve, at least one of iron, cobalt, nickel, copper, manganese, vanadium, zinc, and mixtures thereof, and an alkali metal. The catalyst is exposed to conditions sufficient to form carbides of either iron or cobalt, and then contacted with the provided carbon and hydrogen sources to produce a hydrocarbon.

The carbon source can include carbon monoxide and carbon dioxide, while the hydrogen source can include hydrogen and water.

The catalyst heat treatments can include heating to a temperature of at least 280° C. under an atmosphere, ranging in pressure from about 2 atmospheres to about 20 atmospheres, comprised of hydrogen and either one of carbon monoxide or carbon dioxide. In some embodiments, the catalyst can be heated to a temperature of at least about 320° C. and no greater than about 450° C. under a similar atmosphere.

In those embodiments including a catalyst with a mixture of cobalt and copper, preferably with copper is present in an amount ranging an amount ranging from about 0.5 wt. % to about 5.0 wt. %, particularly preferred is a copper loading of about 2.4 wt. %, the hydrocarbon species produced under CO hydrogenation conditions include alpha-hydroxy acids, such as, 4-hydroxybutanoic acid, 5-hydroxypentanoic acid, and also heterocyclic compounds, such as, tetrahydro-2H-pyran-2-one, and tetrahydro-4-methyl-2H-pyran-2-one.

In the present application, oxidative OMS-2 supported Fe and Co catalysts have been disclosed for CO and $CO_2$ hydrogenation. The unique structure and compositions of OMS-2 can provide three active components (such as, K, Mn, and Fe or Co) as Fischer-Tropsch catalysts. After reduction, HRTEM-EDS and FESEM images show that these components form nanostructural catalysts: a thin layer of Fe or Co on the manganese oxide support. $K_2O$ is gradually released to the interfaces of Fe or Co and manganese oxide supports. In situ XRD studies have shown a phase transformation of OMS-2, Fe or Co, and $K_2O$ to MnO, $Fe_3C$ or $Co_3C$, and $KHCO_3$, respectively. $\theta$-$Fe_3C$, $Co_3C$, and $KHCO_3$ are formed under an elevated temperature and high-pressure $CO/H_2$ mixture.

One preferred embodiment of the presently disclosed catalyst is composed of $Fe_3C$, $KHCO_3$, and MnO and has demonstrated high CO conversion activity (87%) and $CO_2$ conversion (45%) with selectivity of up to 75% toward $C_{2+}$ carbon chains. Liquid products like jet fuel ($C_8$-$C_{15}$), $C_2$-$C_6$ carboxylic acids, and $\alpha$-hydroxy acids can be selectively produced on the oxidative manganese oxide supports. The present catalysts have also shown good stability during a 144 h time-on-stream tests.

In the present disclosure, in situ X-ray diffraction (XRD) under similar conditions of the FT synthesis has been used to identify the phase transformations under dynamic reaction conditions. High-resolution transmission electron microscopy (HRTEM), field emission electron microscopy (FESEM), and energy dispersive spectroscopy (EDS) show the catalyst nanostructure, components, and their interfaces. Combined with gas chromatography (GC), mass spectroscopy (MS), and nuclear magnetic resonance (NMR) techniques, these studies have led to the presently disclosed OMS-2 supported catalysts.

As used herein, "CAT A" refers to a Co/Cu catalyst deposited on a K-OMS-2 support; "CAT B" refers to a Co catalyst deposited on a K-OMS-2 support; "CAT C" refers to an Fe catalyst with 5.4 wt. % K present on a K-OMS-2 support, and "CAT D" refers to an Fe catalyst with 0.7 wt. % K present on a K-OMS-2 support.

When Fe—K-OMS-2 catalysts are reduced in $H_2$ or CO, Fe or $Fe_3C$ nanoparticles formed on the $MnO_x$ (mainly MnO) surface (see FIG. 3). $K_2O$ promoters also gradually migrated to the $MnO_x$ surface, and then formed $KHCO_3$ in $CO/H_2$ atmosphere.

Similar processes are involved in the reduced $Co_3O_4$ (CuO)/K-OMS-2 catalysts. Hcp Co and $K_2O$ were formed on the $MnO_x$ surface. Hcp Co can convert into fcc Co at high temperatures (300-450° C.) due to a small energy gap (0.03 eV), and both hcp Co and fcc Co form $Co_3C$ in $CO/H_2$. Co nanoparticles are easier to oxidize by air or $H_2O$ than Fe nanoparticles, and therefore, these reduced FT catalysts should be kept in an oxygen free dry environment.

The molar ratios of Fe/Mn and Co/Mn in the OMS-2 supported Fe and Co catalysts can be increased by adding more $Fe(NO_3)_3$ or $Co(NO_3)_2$ in the IWI process. In pure OMS-2, the maximum molar ratio of Fe/Mn in the catalysts is 1/5 because an excess of iron will lead to secondary phases in the framework doped Fe—K-OMS-2. The maximum molar ratio of K/Mn (1/8) in the OMS-2 support is determined by the formula $KMn_8O_{16}$ (K-OMS-2). Potassium oxide ($K_2O$) is formed during the reduction of K-OMS-2. It is noted that pure $K_2O$ decomposes at 350° C., and while other metal oxides can stabilize $K_2O$ in the catalysts, some $K_2O$ can be lost during calcination of the OMS-2 supported catalysts at elevated temperatures (>450° C.). As-synthesized hydrothermal Fe—K-OMS-2 contained 5.4% of K after reduction in $H_2$/He, higher more than the HT Fe—K-OMS-2 (0.7% K) prepared by a high temperature ("HT") method set forth herein.

In situ XRD patterns (FIGS. 4, 5, 10, 11) show that the formation of carbides and $KHCO_3$ is determined by the reaction temperature. Apparent XRD peaks of carbides ($Co_2C$, $Co_3C$, $Fe_3C$, and $Fe_{2.5}C$) and $KHCO_3$ are present at 220° C., and the corresponding catalysts have low activity in $CO_2$ and CO hydrogenation (FIG. 6A). Co catalysts have higher activity than Fe catalysts at low temperature (220° C.). The intensity of carbide peaks keeps increasing until 320° C., indicating the formation of more carbides. The conversion of CO and $CO_2$ also kept increasing with temperature. The catalytic activity of the Fe catalysts is greater than the CoCu catalysts at 280° C. FIG. 6B shows that the CO and $CO_2$ hydrogenation reactions experienced an induction stage and reached a maximum conversion due to the gradual formation of active carbide phases. The $H_2$/He reduced OMS-2 supported Fe catalysts (CAT C) have very limited activity in the beginning of $CO_2$ hydrogenation (FIG. 6A).

Formation of carbides in the presently disclosed catalysts is desirable to achieve a catalyst active for FT synthesis. Under $CO_2$ hydrogenation conditions, the extra step of the reverse water-gas shift ("RWGS") reaction (see Eq. 1) forms CO which then forms the carbides. The formation of carbides is determined by the concentrations of adsorbed $[H]_{ad}$ and $[CO]_{ad}$ on the catalyst surfaces, which are determined, in turn, by the partial pressures of $H_2$ and CO and the nature of the catalysts. Fewer $Fe_{2.5}C$ (or $Co_2C$ and $Co_3C$) carbides are formed in the $CO_2/H_2$ mixtures, while more $Fe_3C$ ($Co_3C$) carbides are formed in the $CO/H_2$ mixtures at 320° C. $CO_2$ adsorption on these catalysts is stronger than CO adsorption on the bulk catalysts as determined by in situ FT-IR (FIG. 15).

In situ XRD patterns (FIGS. 4h, 5i, 10 and 11 24 h) show four catalysts with various Co and Fe carbides and they are listed in Table 2. These active catalysts are stable after 24 h reaction. FIGS. S5-S6 indicate that the Fe and Co carbides and $KHCO_3$ do not change in $CO_2$ hydrogenation. Therefore, the type and amount of bulk iron (or cobalt) carbides can be controlled in $CO_2$ hydrogenation.

Table 2 shows that the $H_2$/CO reduced Co and Fe catalysts have 3 and 2.5 times conversion of $CO_2$ than the $H_2/CO_2$ reduced Co and Fe catalysts, respectively. These carbide catalysts have shown high selectivity (up to 75%) towards $C_{2+}$ carbon chains with a high $CO_2$ conversion rate (45%). $Fe_3C$ and $Co_3C$ are apparently the most active phases among the listed species and $Fe_3C$ carbide-containing catalysts are very efficient catalysts towards long chain hydrocarbons. $H_2/CO_2$ reduced Co and Fe catalysts can still contain some metallic particles, and these metallic catalysts may account for the high selectivity to CO and $CH_4$.

Manganese has a wide range of possible oxidation states ($2^+$, $3^+$, and $4^+$) determined by the reduction temperature in the OMS-2 support. TPR-MS spectra (FIG. 8) of the K-OMS-2 support show that the manganese in OMS-2 changed its valences at three temperatures of about 250, 310, and 415° C. due to loss of lattice oxygen during CO/He reduction. The corresponding valences of manganese in OMS-2 catalysts changed in the order of $Mn^{4+} \rightarrow Mn^{3+} \rightarrow Mn^{2+}$. The oxidation activity also decreased in this order.

In some embodiments of the present teachings, the catalyst reduction temperature can be varied to change the species of hydrocarbon products. As set forth in FIG. 13, the reduction temperature was increased from 350 to 450° C., which results in $MnO_2$ in the K-OMS-2 support being fully reduced to less oxidative MnO, and longer chain hydrocarbons are produced in this reaction sequence. These oxidative $MnO_x$ supports are capable of selectively producing light alkenes ($C_2$-$C_6$) from $CO_2$ (or CO) hydrogenation using OMS-2 supported Fe and Co catalysts.

According to present theory, the following mechanisms may proceed under $CO_2$ hydrogenation conditions. Adsorbed $CO_2$ are transformed into CO on the supported Co and Fe catalysts via the RWGS reaction (Eq. 1). $CH_2^*$ radicals are generated from the hydrogenation of CO on the supported Co and Fe catalysts (Eq. 2). One pathway involves carbon chain growth on the metallic phases and metal carbides. Another pathway of carbon chain growth is that $CH_2^*$ reacts with intermediate $KHCO_2$ (formic acid potassium) and the carbon chain continues to grow with the insertion of more $CH_2^*$ (Eqs. 5-6). $KHCO_2$ species were formed on the supported Co and Fe catalyst surface via Eq. 4. It is believed that under higher (450° C.) reduction, the intermediate $KHCO_2$ is further reduced. Due to existing $Mn^{3+}$ and $Mn^{4+}$ ions in low temperature (350° C.) reduced Co catalysts, $CH_2^*$ radicals are more likely to follow the second pathway to form carboxylic acids. Moreover, the products of the first pathway may be oxidized by $Mn^{x+}$ (x=3-4) to carboxylic acids, and the chance of growth of long hydrocarbon chains via the first pathway is low. The liquid products are 100% $C_2$-$C_6$ carboxylic acids (FIG. 13A).

$$CO_2(g) + H_2(g) \leftrightarrow CO(g) + H_2O(g) \qquad (1)$$

$$CO(g) + 2H_2(g) \leftrightarrow CH_2^*(ad) + H_2O(g) \qquad (2)$$

$$K_2O(s) + 2CO_2(g) + H_2O(g) \leftrightarrow 2KHCO_3(s) \qquad (3)$$

$$KHCO_3(s) + H_2(g) \leftrightarrow KHCO_2(s) + H_2O(g) \qquad (4)$$

$$KHCO_2(s) + CH_2^*(ad) \leftrightarrow CH_3COOK(s) \qquad (5)$$

$$CH_3COOK(s) + nCH_2^*(ad) \leftrightarrow CH_3(CH_2)_nCOOK(s) \qquad (6)$$

$$R-K(s) + H_2O(g) + CO_2(g) \leftrightarrow RH(g) + KHCO_3(s) \qquad (7)$$

(R=$CH_3COO^-$, $CH_3(CH_2)_nCOO^-$, n=1 to 4)

In the present disclosure, in situ XRD patterns show the high-pressure induced growth of single $KHCO_3$ crystals from potassium oxide under FT synthesis conditions. It has been reported by others that addition of potassium, such as $K_2CO_3$, $K_2C_2O_4$, and KOH, promoted long carbon chain growth and reduced the formation of methane in the FT synthesis. In the method of the present disclosure, single $KHCO_3$ crystals form from potassium oxide in high-pressure $CO/H_2$ mixtures. $KHCO_3$ crystals do not form at low pressure (1 atm), and form less in high-pressure $CO_2/H_2$ mixtures. This suggests that added potassium may also convert to $KHCO_3$ crystals under the FT reaction conditions. Small $KHCO_3$ crystals (<80 nm)

show good promotion effect, and large KHCO$_3$ crystals (294 nm) may actually decrease the catalytic activity of the catalysts (FIG. 6B). Tables 1 and 3 show that the OMS-2 supported Fe catalysts containing 5.4% K and carbide, Fe$_3$C, significantly decreased CH$_4$ formation from 52% to 15%. The KHCO$_3$ promoters may decrease the CH$_4$ formation activity due to competing adsorption of CO and H$_2$. According to present theory, and in contrast to previous potassium promotion studies, the K-OMS-2 support may gradually release K$^+$ ions to the catalyst surface to compensate for the loss of K$^+$ at the catalyst surface. This controlled release of K$^+$ prevents overly high enrichment of KHCO$_3$ which can, in turn, hinder the adsorption of CO and H$_2$.

For some embodiments of the present teachings, Cu dopants are added to the OMS-2 supported CoCu catalysts to shift the products from carboxylic acids to α-hydroxy acids. Ethanoic acid and propanoic acid were produced on the OMS-2 supported Co catalysts. According to present theory, 4-hydroxybutanoic acid can be formed from CH$_3$OH and propanoic acid via the aldol condensation (Eq. 8):

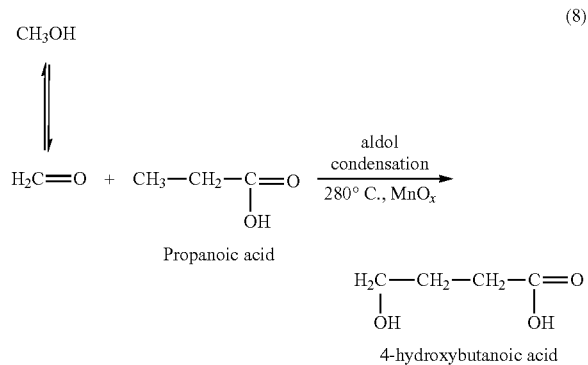

(8)

Tetrahydro-2H-pyran-2-one can be formed from 5-hydroxy-pentanoic acid via the intermolecular condensation (Eq. 9). 5-hydroxy-pentanoic acid and tetrahydro-4-methyl-2H-pyran-2-one can be formed via a similar aldol condensation and intermolecular condensation.

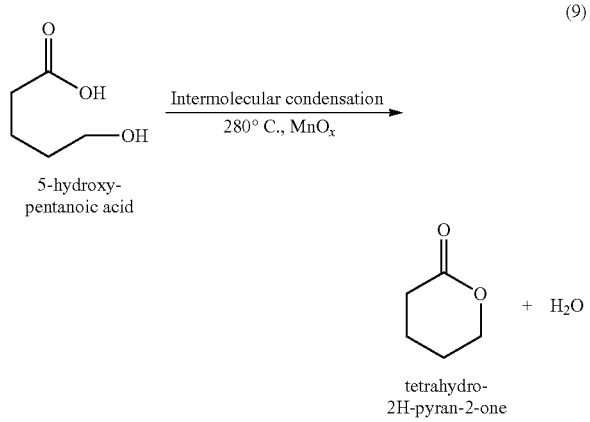

(9)

According to the present disclosure, α-hydroxy acids were formed along with C$_2$-C$_3$ carboxylic acids when 2.4 wt. % of Cu was doped into the OMS-2 supported Co catalysts (CAT A) (see FIG. 14). The liquid product molar ratio of acetic acid, propanoic acid, 4-hydroxybutanoic acid, 5-hydroxy-pentanoic acid, tetrahydro-2H-pyran-2-one, and tetrahydro-4-methyl-2H-pyran-2-one, is 63:18:4:8:5:2.

In some embodiments of the present disclosure, potassium promotion, with for instance KHCO$_3$, enhances the activity and selectivity of the OMS-2 supported catalysts towards highly desirable long carbon chain hydrocarbons in both CO$_2$ and CO hydrogenation processes. Catalysts reduced at temperatures of 400-450° C. produced long carbon chain hydrocarbons as discussed above. Compared with the OMS-2 supported Co catalysts reduced at the same temperatures, the Fe catalysts show much higher activity, and longer carbon chain hydrocarbons and less oxygenates were produced. The increased performance of the Fe catalyst is presently believed to be largely dependent on the enhanced RWGS activity of the Fe catalysts over the Co catalysts. Table 4 shows that the CO hydrogenation products of the presently disclosed OMS-2 Fe catalyst contains higher amounts of alkenes (2 times) and aldehydes (3 times), and fewer aromatics (0.5 time) than Co/Al$_2$O$_3$ catalysts.

In the presently disclosed method, the reduction temperature of the catalysts impacts the selectivity of the products (see FIG. 13). K-OMS-2 supported Co catalysts (CAT B) reduced at a low temperature of 350° C. underwent CO$_2$ hydrogenation, the liquid products were ethanoic acid (53 molar %), propanoic acid (27%), butanoic acid (14%), and pentanoic acid (6%). The gas products were CH$_4$ (38%), CO (19%), C$_2$H$_6$ (16%), and C$_3$-C$_7$ olefins (21%). Aldehydes and other hydrocarbons were not detected by GC-MS in the liquid products. When CAT C was reduced at the high temperature of 450° C., the liquid products of CO$_2$ hydrogenation are jet fuel (C$_8$-C$_{20}$), and 67% of the jet fuel is alkenes.

Typical Fischer-Tropsch products using Co/Al$_2$O$_3$ catalysts are mainly paraffins and few olefins, including small fractions of linear and branched alcohols, ketones, carboxylic acids, and linear aldehydes. According to the presently taught method, the products show a different distribution of aldehydes, aromatics, alkenes, and alkanes from typical FT products. As shown in Table 4, for CAT C, the molar ratio of aldehydes/aromatics/alkenes for CO hydrogenation is 1:2:45, compared with 1.0:1.5:3.5 for CO$_2$ hydrogenation. The same ratio for the Co/Al$_2$O$_3$ catalysts in CO hydrogenation is 1:13:67. Note that CO$_2$ hydrogenation using the Co/Al$_2$O$_3$ catalysts did not produce these liquid products. The low concentrations of aromatics (2%) and aldehydes (1%) present in the CO hydrogenation products of the OMS-2 supported Fe catalysts (CAT C), while the CO$_2$ hydrogenation with the same catalysts produced significant amounts of aldehydes (12%) and aromatics (18%) is attributed to the strong CO$_2$ adsorption which hinders H$_2$ adsorption on these catalysts as described herein.

FIG. 7 shows that the gaseous products of CO and CO$_2$ hydrogenation using the OMS-2 supported Fe and Co catalysts are mainly C$_2$-C$_7$ light hydrocarbons. GC data shows that the ratio of an alkene (e.g C$_3$H$_6$) to an alkane (C$_3$H$_8$) is up to 10:1. More desirable C$_2$-C$_6$ alkenes are selectively produced. This carbon chain growth toward long chains (C$_{2+}$) on the supported Fe catalysts is clearly shown in FIGS. 7A and B in both CO and CO$_2$ hydrogenation. In contrast, the long carbon chain growth on supported Co catalysts is more difficult than on supported Fe catalysts. Jet fuel (C$_7$-C$_{15}$) has been produced with high selectivity using the OMS-2 supported Fe catalysts in CO and CO$_2$ hydrogenation, respectively.

Typically light products (C$_2$-C$_7$) are the main products of the OMS-2 supported catalysts with solid wax products are less than 2% of the weight of the total products. However, under specific conditions of a high concentration (>20 wt. %) of cobalt or iron on manganese oxide supports and a low gas hourly space velocity, the chance of growth of long carbon chains increases. The carbon number can reach 45, and most products are straight chain hydrocarbons including olefins and paraffins (see FIG. 12).

EXAMPLES

Catalysts Preparation and Characterization

The synthesis of OMS-2 supports has been described elsewhere; see U.S. Pat. Nos. 5,702,673 and 7,767,770, the disclosures of which are incorporated by reference herein in their entireties for all purposes.

The OMS-2 supported cobalt catalysts were synthesized by an IWI method. Cobalt (II) nitrate (Co/Mn: 0.2, all in molar ratio) and copper nitrate (Cu/Co: 0.1 molar ratio) were dissolved in deionized (DI) water, and then OMS-2 was added into the cobalt nitrate solution under agitation for 2 h. The cobalt loading can range from about 10 to about 25 wt. %. The impregnated samples were dried at 80° C. in flowing air for 4 h, then at 120° C. for 2 h, and finally calcined in flowing air (200 cm$^3$/min) at 450° C. for 6-12 h with a ramp rate of 2° C./min using a tube furnace. OMS-2 supported CoCu catalysts (CAT A) and OMS-2 supported Co catalysts (CAT B) were synthesized following the above procedures except that no copper nitrate was added during the CAT B preparation.

In some instances, the Co/Cu containing catalyst can be produced by CVD coating of a Co K-OMS-2 catalyst with Cu(acac)$_2$ utilized as the copper precursor in the CVD reactor.

Framework doping of Fe$^{3+}$ ions in OMS-2 (Fe—K-OMS-2) occurred by conversion from Fe—K-birnessite. MnCl$_2$.4H$_2$O (0.2 mol) was dissolved in 150 mL of DI water. FeCl$_3$ was added into the solution for an Fe/Mn atomic ratio of 1/5 at room temperature under agitation. Oxygen (500 cm$^3$/min) was bubbled into the solution. NaOH solution (100 mL of 5 M) was added dropwise into the solution. After stirring for 2 h, the product was filtered, washed, and then transferred to a 250 mL KCl solution (1 M) for ion-exchange at room temperature (RT) under stirring for 12 h. The Fe, K-birnessite was then washed with DI water.

Two Fe—K-OMS-2 samples with 5.4% and 0.7% K, respectively, were synthesized using a hydrothermal method and a high temperature calcination method, respectively. For the hydrothermal synthesis, 70 mL DI water, 0.15 mol K$_2$SO$_4$, and 0.2 mol Fe—K-birnessite were mixed in an autoclave. The autoclave was sealed in an acid digest bomb and placed in an oven at 180° C. for 24 h. As-synthesized Fe—K-OMS-2 products (CAT C) were washed and dried at 120° C. for 12 h.

For high temperature ("HT") calcination syntheses, Fe—K-birnessite (0.2 mol) was calcined stepwise in oxygen (200 cm$^3$/min) at 120, 200, 350, 500, and 625° C. for 2 h in a tube furnace. As-synthesized HT Fe—K-OMS-2 (CAT D) was obtained.

Powder XRD was performed with a Scintag XDS 2000 X-ray diffractometer equipped with a Cu Kα X-ray source (λ=1.54 Å). Field emission scanning electron microscopy (FESEM) was performed using a Zeiss DSM 982 Gemini FESEM instrument with a Schottky emitter. Transmission electron microscopy (TEM) images were obtained using a JEOL 2010 FasTEM at accelerating voltages of 200 kV with an energy dispersive spectroscopy (EDS) system. A Micromeritics ASAP 2010 instrument was used to measure the surface area using nitrogen adsorption at −196° C. Temperature programmed reduction-mass spectrometry (TPR-MS) analysis was performed with a designed setup and an MKS-UT1 PPT quadrupole mass spectrometer.

Hydrogenation of CO and CO$_2$

Hydrogenations of CO$_2$ or CO were performed in a packed bed reactor at temperatures of 120-320° C. and a pressure of 13.6 atm. Pre-mixed CO$_2$/H$_2$/Ar (Gas 1, molar ratio: 3:6:1) and CO/H$_2$/Ar (Gas 2, 3:6:1) gas mixtures (Airgas) were used for FT syntheses. Ar was utilized as an internal standard for GC analysis. 0.75 g catalysts were loaded into a packed stainless tube reactor (ID 0.9 cm). The catalysts were reduced in 10% CO (or H$_2$)/He at a pressure of 1 atm and temperatures of 350-450° C. with a ramp rate of 2° C./min for 2 h. The reactor was then cooled below 100° C., and the feed gases (30-200 cm$^3$/min) were switched to Gas 1 or Gas 2. A tube furnace was heated at a ramp rate of 5° C./min to the reaction temperature (200-360° C.).

In Situ XRD Measurements

The in situ XRD studies were performed under similar conditions of hydrogenation of CO and CO$_2$ on a XTRA X-ray diffractometer (Cu K$_α$ radiation) equipped with an Anton Parr XRK 900 heater chamber (max. pressure, 10 atm). The same pre-mixed gases for the FT synthesis were used for in situ XRD. The heating rate was 2° C./min; the total pressure was 1 atm for the H$_2$/He reduction and 8.5 atm for the hydrogenation of CO and CO$_2$; and the gas flow rate was 40 cm$^3$/min. In situ XRD patterns were obtained by step scanning over the angle range 2θ=5~80° at an increment of 1.2°/min and at an accumulation time of 0.5 s at each point. To calculate the average crystallite size, LaB$_6$ was used as an external standard for the instrumental full width at half maximum (FWHM) calibration. XRD of LaB$_6$ was operated under identical conditions as that of the OMS-2 supported Fe and Co catalysts.

Product Analyses

Gaseous products were analyzed using an online GC (SRI 8610C) equipped with two detectors in series (a flame ion detector for hydrocarbons (>1 ppm) and a thermal conductivity detector for CO, CH$_4$, CO$_2$, and Ar (>300 ppm)) and two columns (molecular sieve 13× and HayeSep D). The initial oven temperature was held at 10° C. for 8 min by adding dry ice in the column chamber, and was then raised to 200° C. at a ramp rate of 10° C./min and heated at 200° C. for 5-20 min. A standard deviation of the GC analysis was about 3-5%.

Liquid products collected from the condensing tank and solid wax collected at the filter were analyzed by GC-MS. The detection limit is about 1-5 ug/L. The standard deviation of GC-MS was about 2-3%. A Hewlett-Packard GC (HP5890 series II) equipped with a mass-selective detector (MSD, HP5971 Series) and a DB-5HT capillary polar column (30 m×0.25 mm). Solid wax products (light yellow) were dissolved in CS$_2$ (HPLC, 99.8%) for GC-MS analyses. Liquid products were diluted in acetonitrile (HPLC, 99%) and 1 μg/mL C$_6$H$_5$F was added as an internal standard for GC-MS analyses. The temperatures of the injector and GC-MSD interfaces were 270 and 280° C., respectively. For wax (liquid) analyses, the initial oven temperature was held at 50° C. for 5 min and then raised to 350° C. (320° C.) at a rate of 5° C./min. The dwell time was 5 min. Liquid products were also analyzed by $^1$H NMR (Bruker DRX-400 400 MHz) using deuterated dimethyl sulfoxide (DMSO-d6) as an internal standard.

Catalyst Structure, Composition, and Morphology

K-OMS-2 nanofibers with a diameter of 20-25 nm and a length of 0.5-5 μm have a surface area of 65 m$^2$/g (FIG. 1). Synthetic K-OMS-2 (KMn$_8$O$_{16}$) has up to 4% (atomic) of K$^+$ ions in its tunnel structure. FIG. 2 shows the XRD patterns of the K-OMS-2 support and three OMS-2 supported Fe and Co catalysts according to the present disclosure. The labeled peaks show that K-OMS-2 is a pure tetragonal phase (JCPDS No. 29-1020) with the cryptomelane-type structure. Framework doped Fe—K-OMS-2 shows an identical structure to that of K-OMS-2. Hydrothermal Fe—K-OMS-2 shows low intensity peaks indicating smaller particles than HT Fe—K-OMS-2. Some unconverted Fe-birnessite existed in CAT C. Its $K^+$ concentration was 5.4%, which is higher than the 4% of K-OMS-2.

After the IWI of $Co(NO_3)_2$ on K-OMS-2 supports, the XRD patterns of CAT B confirmed that $\alpha$-$Co(NO_3)_2 \cdot 6H_2O$ (JCPDS No. 25-1219) was coated on the K-OMS-2 supports. $Co(NO_3)_2$ was decomposed to $Co_3O_4$ on K-OMS-2 supports after calcination at 450° C. $Cu(NO_3)_2$ was added to $Co(NO_3)_2$ in the IWI process for the preparation of CAT A. $Cu(NO_3)_2$ was decomposed to CuO after calcination.

Fe—K-OMS-2, $Co_3O_4$/K-OMS-2, and $Co_3O_4$/CuO/K-OMS-2 catalyst precursors are not active and must be reduced before FT synthesis. After reduction in 20% $H_2$/He (balance), $CO_3O_4$ was reduced to hexagonal close packed (hcp) and face-center cubic (fcc) Co nanoparticles; CuO was reduced to fcc Cu; and K-OMS-2 was reduced to cubic MnO (JCPDS No. 7-230) (FIG. 4a). The crystallite size of Co nanoparticles along the [101] direction, calculated from the Sherrer Equation, is 42 nm. Typical elemental maps of four reduced catalysts (CAT A, B, C, and D) showed uniform elemental distribution for each Co, Mn, K, and Cu element.

FIG. 3 shows the TEM image and EDX spectra of the reduced OMS-2 supported Co and Fe catalysts. The TEM image (FIG. 3A) of CAT B shows the cubic spinel $Co_3O_4$ (JCPDS No. 42-1467) phase and the hexagonal close-packed (hcp) Co phase present in the CAT B catalyst. The TEM image (FIG. 3B) of CAT D shows that the distance between the lattice fringes is 2.0 Å, which is close to the d-spacing (2.03 Å) of the (110) planes of $\alpha$-Fe in the XRD data.

In Situ XRD Analyses

FIG. 4a shows that the in situ XRD pattern of the reduced CAT C has a small peak at a $2\theta$ of 44.6°, which is assigned to $\alpha$-Fe (body-centered cubic (bcc), JCPDS No. 6-696) and other five major peaks ($2\theta$: 34.9, 40.6, 58.7, 70.2, and 73.6°) were assigned to cubic MnO. When the temperature was increased to 220° C. in CO hydrogenation, two broad peaks at $2\theta$ of 31.2 and 51.6° appeared, indicating $KHCO_3$ (Kalicinite, JCPDS No. 12-292) was formed. With the temperature increased to 320° C. for 15 minutes, the $Fe_3C$ (Cohenite, JCPDS No. 35-772) phase was observed at $2\theta$ of 37.8°, 41.4°, and 45.3°. A small $Fe_2C$ peak was also seen at a $2\theta$ of 28.2°. The particle sizes of $Fe_3C$, $KHCO_3$, and MnO crystals exposed to reactants at different reaction times were calibrated from the Sherrer Equation. After a 24 h reaction, the $Fe_3C$ crystals along the [031] direction grew from 8 nm at 220° C. to 60 nm at 320° C.; $KHCO_3$ crystals along the [−311] direction grew from 5 nm at 120° C. to 81 nm at 320° C. (see Table 1); the MnO crystallite size decreased from 22 nm at room temperature to 13 nm at 320° C. due to the etching of acidic products and $KHCO_3$. FT-IR data (FIG. 17) of the post-reaction Fe and Co catalysts further confirmed the formation of $KHCO_3$. The FESEM images (FIGS. 1C and D) show the morphology of post-reaction catalysts of CAT C. The $Fe_3C$ phase is clearly shown in the black deposit and Fe—K-OMS-2 nanofibers were broken into smaller fibers and particles likely due to etching of acidic products and diffusion of $K^+$ ions.

The in situ XRD pattern (FIG. 5a) of the reduced CAT A shows hcp cobalt (JCPDS No. 5-727) peaks at $2\theta$ of 41.4, 47.3, and 75.4°, fcc cobalt (JCPDS No. 15-806) peaks at $2\theta$ of 44.2 and 51.6°, and cubic copper peaks (JCPDS No. 4-836) at a $2\theta$ of 43.1°. The formation of orthorhombic $Co_3C$ (JCPDS No. 26-450) was observed in XRD patterns. After the temperature was increased to 320° C. for 15 mins, the $Co_3C$ peaks were clearly seen at $2\theta$ of 42.6, 56.6, 71.6 and 76.3°. After a 24 h reaction, the crystallite size of $Co_3C$ showed an increase from 23 nm to 39 nm along [103] direction; the crystallite size of hcp cobalt decreased from 42 nm to 9 nm; the crystallite size of copper decreased from 86 nm to 75 nm; and the crystallite size of MnO decreased from 40 nm at room temperature to 29 nm at 320° C. $KHCO_3$ crystals along the [−311] direction grew from 2 nm at 120° C. to 294 nm at 320° C. after a 24 h reaction (Table 1). The increased size of $KHCO_3$ crystals is believed to be due to less water formation for Co catalysts than for Fe catalysts. FIG. 1B shows the morphologies of different phases in CAT A. Dark carbon species are shown on the catalyst surface.

The in situ XRD patterns (FIG. 10) of CAT C in $CO_2$ hydrogenation show that $\alpha$-Fe gradually transformed to x-$Fe_{2.5}C$ (JCPDS No. 36-1248) with the temperature increasing from room temperature to 320° C. A small decrease in the crystallite size of the MnO support along the [111] direction was found. The in situ XRD patterns (FIG. 11) of $CO_2$ hydrogenation using the OMS-2 supported Co and Cu catalysts show that the crystallite size of hcp Co increased from 5 nm at room temperature to 18 nm at 320° C., indicating the sintering of nanoparticles. The crystallite sizes of Cu and MnO have slightly decreased. Compared to large $KHCO_3$ crystals (75-300 nm) formation in CO hydrogenation (Table 1), only small $KHCO_3$ crystals (6-12 nm) were formed in $CO_2$ hydrogenation.

All publications, articles, papers, patents, patent publications, and other references cited herein are hereby incorporated by reference herein in their entireties for all purposes.

Although the foregoing description is directed to the preferred embodiments of the present teachings, it is noted that other variations and modifications will be apparent to those skilled in the art, and which may be made without departing from the spirit or scope of the present teachings.

The examples are presented herein to provide a more complete understanding of the present teachings. The specific techniques, conditions, materials, and reported data set forth to illustrate the principles of the present teachings are exemplary and should not be construed as limiting the scope of the present teachings.

The foregoing detailed description of the various embodiments of the present teachings has been provided for the purposes of illustration and description. It is not intended to be exhaustive or to limit the present teachings to the precise embodiments disclosed. Many modifications and variations will be apparent to practitioners skilled in this art. The embodiments were chosen and described in order to best explain the principles of the present teachings and their practical application, thereby enabling others skilled in the art to understand the present teachings for various embodiments and with various modifications as are suited to the particular use contemplated. It is intended that the scope of the present teachings be defined by the following claims and their equivalents.

TABLE 1

The crystallite sizes of KHCO$_3$ with increasing time and temperatures in CO hydrogenation using the OMS-2 supported Fe and CoCu catalysts.

| Catalyst | 25° C. | 120° C. | 220° C. | 320° C. 15 min | 320° C. 2 h | 320° C. 8 h | 320° C. 16 h | 320° C. 24 h |
|---|---|---|---|---|---|---|---|---|
| KHCO$_3$ [−311] in CAT C | NA | 5 ± 0.3 | 12 ± 0.4 | 52 ± 2 | 69 ± 2 | 73 ± 2 | 81 ± 2 | 81 ± 2 |
| KHCO$_3$ [−311] in CAT A | NA | 2 ± 0.1 | 8 ± 0.4 | 54 ± 2 | 79 ± 2 | 102 ± 3 | 128 ± 4 | 294 ± 9 |

Note:
The unit of the crystallite size is nm. NA represents "below the detection limit".

TABLE 2

Catalytic activity and product distribution of the OMS-2 supported catalysts in CO$_2$ hydrogenation

| Catalysts | Active phase | CO$_2$ Conv. (%) | Selectivity (%) | | | |
|---|---|---|---|---|---|---|
| | | | CO | CH$_4$ | C$_2$-C$_4$ | C$_{5+}$ |
| H$_2$/CO$_2$ reduced CAT C | Fe$_{2.5}$C | 18 ± 0.5 | 41 ± 1.2 | 34 ± 1.0 | 21 ± 0.6 | 4 ± 0.1 |
| H$_2$/CO reduced CAT C | Fe$_3$C | 45 ± 1.4 | 19 ± 0.6 | 15 ± 0.5 | 21 ± 0.6 | 44 ± 1.3 |
| H$_2$/CO$_2$ reduced CAT A | Co$_2$C, Co$_3$C, Co | 14 ± 0.4 | 33 ± 1.0 | 31 ± 0.9 | 28 ± 0.8 | 8 ± 0.2 |
| H$_2$/CO reduced CAT A | Co$_3$C (few Co) | 42 ± 1.3 | 19 ± 0.6 | 6 ± 0.2 | 47 ± 1.4 | 28 ± 0.8 |

Note:
The reaction conditions are the same as FIG. 6B, and the reaction time is 1 h.

TABLE 3

CO$_2$ conversion and selectivity of the OMS-2 supported Fe catalysts with different K concentration

| Catalysts | CO$_2$ Conv. (%) | Selectivity (%) | | | |
|---|---|---|---|---|---|
| | | CO | CH$_4$ | C$_2$-C$_4$ | C$_{5+}$ |
| CAT C (5.4% K) | 45 ± 1.4 | 19 ± 0.6 | 15 ± 0.5 | 21 ± 0.6 | 44 ± 1.3 |
| CAT D (0.7% K) | 42 ± 1.3 | 13 ± 0.8 | 52 ± 1.6 | 30 ± 0.9 | 5 ± 0.2 |

Note:
The conditions are the same as Table 2.

TABLE 4

Comparisons of aldehydes, aromatics, and alkenes distributions in liquid products of CAT C and Co/Al$_2$O$_3$ reference catalysts

| Catalysts | Feeding gas molar ratio | Selectivity (%) | | | |
|---|---|---|---|---|---|
| | | Aldehydes | Aromatics | Alkenes | Alkanes |
| CAT C | CO$_2$/H$_2$ = 1:2 | 12 ± 0.4 | 18 ± 0.5 | 42 ± 1.3 | 28 ± 0.8 |
| CAT C | CO/H$_2$ = 1:2 | 1.0 ± 0.1 | 2 ± 0.1 | 45 ± 1.4 | 52 ± 1.6 |
| Co/Al$_2$O$_3$ | CO/H$_2$ = 1:2 | 0.3 ± 0.1 | 4.3 ± 0.2 | 22 ± 0.7 | 73 ± 2.2 |

Note:
These data are $^1$H NMR results.

What we claim is:

1. A catalyst comprising manganese oxide-containing catalyst support material derived from manganese oxide-containing octahedral molecular sieves, at least one of iron carbide, cobalt carbide, and mixtures thereof, and an alkali metal.

2. The catalyst according to claim 1, wherein the iron carbide comprises Fe$_3$C.

3. The catalyst according to claim 1, wherein the cobalt carbide comprises Co$_3$C.

4. The catalyst according to claim 1, wherein the alkali metal comprises potassium, and is present in an amount ranging from about 0.5 wt. % to about 7.5 wt. %.

5. The catalyst according to claim 4, wherein the potassium is present in an amount ranging an amount ranging from about 4.0 wt. % to about 6.0 wt. %.

6. The catalyst according to claim 1, wherein the catalyst further comprises cobalt carbide and copper, and the copper is present at Cu:Co molar ratio ranging from about 0.01:1 to about 0.5:1.

7. The catalyst according to claim 1, wherein iron carbide is present at a Fe:Mn molar ratio of no greater than 1:5.

8. The catalyst according to claim 1, wherein the alkali metal is present at an alkali metal:Mn molar ratio of no greater than 1:8.

9. The catalyst according to claim 1, wherein the alkali metal comprises potassium present as potassium hydrogen carbonate.

10. A catalyst comprising a manganese oxide-containing support material prepared by heat treatment of octahedral molecular sieves, at least one of iron carbide, cobalt carbide, and mixtures thereof, and an alkali metal.

11. The catalyst according to claim 10, wherein the heat treatment comprises heating the octahedral molecular sieves to a temperature of at least 450° C. in an atmosphere.

12. The catalyst according to claim 10, wherein the atmosphere comprises of a mixture of H$_2$ and either one of CO or CO$_2$.

13. The catalyst according to claim 10, wherein the heat treatment comprises heating the octahedral molecular sieves to a temperature and for a duration in an atmosphere sufficient to transform the octahedral molecular sieves to a mainly manganese oxide-containing support material.

14. The catalyst according to claim 10, wherein the atmosphere comprises of a mixture of $H_2$ and either one of CO or $CO_2$.

15. The catalyst according to claim 10, wherein the iron carbide comprises $Fe_3C$.

16. The catalyst according to claim 10, wherein the cobalt carbide comprises $Co_3C$.

17. The catalyst according to claim 10, wherein the alkali metal comprises potassium, and is present in an amount ranging from about 0.5 wt. % to about 7.5 wt. %.

18. The catalyst according to claim 17, wherein the potassium is present in an amount ranging an amount ranging from about 4.0 wt. % to about 6.0 wt. %.

19. The catalyst according to claim 10, wherein the catalyst further comprises cobalt carbide and copper, and the copper is present at Cu:Co molar ratio ranging from about 0.01:1 to about 0.5:1.

20. The catalyst according to claim 10, wherein iron carbide is present at a Fe:Mn molar ratio of no greater than 1:5.

21. The catalyst according to claim 10, wherein the alkali metal is present at an alkali metal:Mn molar ratio of no greater than 1:8.

* * * * *